US007940972B2

(12) United States Patent
Wildes et al.

(10) Patent No.: US 7,940,972 B2
(45) Date of Patent: May 10, 2011

(54) SYSTEM AND METHOD OF EXTENDED FIELD OF VIEW IMAGE ACQUISITION OF AN IMAGED SUBJECT

(75) Inventors: Douglas G. Wildes, Ballston Lake, NY (US); Warren Lee, Niskayuna, NY (US); Terry M. Topka, Scotia, NY (US); Weston B. Griffin, Niskayuna, NY (US)

(73) Assignee: General Electric Company, Scheneltady, NY (US)

( * ) Notice: Subject to any disclaimer, the term of this patent is extended or adjusted under 35 U.S.C. 154(b) by 677 days.

(21) Appl. No.: 12/099,862

(22) Filed: Apr. 9, 2008

(65) Prior Publication Data

US 2008/0285824 A1 Nov. 20, 2008

Related U.S. Application Data

(60) Provisional application No. 60/938,445, filed on May 16, 2007.

(51) Int. Cl.
*G06K 9/00* (2006.01)
*A61N 5/00* (2006.01)

(52) U.S. Cl. ........ 382/128; 382/103; 382/153; 382/294; 850/1; 600/11; 600/459

(58) Field of Classification Search .................. 382/103, 382/106, 107, 128–132, 153–154, 294; 850/1–8, 850/21–61; 600/11, 459, 462
See application file for complete search history.

(56) References Cited

U.S. PATENT DOCUMENTS

| | | | | |
|---|---|---|---|---|
| 3,628,012 A * | 12/1971 | Hosoki et al. | ................. | 250/307 |
| 3,794,762 A * | 2/1974 | Zukerman et al. | ............. | 348/34 |
| 3,795,808 A * | 3/1974 | Drayton et al. | ................ | 250/310 |
| 3,979,594 A * | 9/1976 | Anger | ............................ | 250/369 |
| 4,020,343 A * | 4/1977 | Shimaya et al. | ............... | 250/310 |
| 4,071,759 A * | 1/1978 | Namae | .......................... | 250/310 |
| 4,431,915 A * | 2/1984 | Nakagawa et al. | ........... | 250/310 |
| 4,572,202 A * | 2/1986 | Thomenius | ................... | 600/443 |
| 4,611,119 A * | 9/1986 | Fazekas et al. | ................ | 250/307 |
| 4,706,681 A | 11/1987 | Breyer et al. | | |
| 4,821,731 A | 4/1989 | Martinelli et al. | | |
| 4,861,984 A * | 8/1989 | West | .............................. | 250/236 |
| 4,896,673 A | 1/1990 | Rose et al. | | |
| 4,991,589 A * | 2/1991 | Hongo et al. | .................. | 600/455 |
| 5,135,001 A | 8/1992 | Sinofsky et al. | | |

(Continued)

OTHER PUBLICATIONS

Kanckstedt, C. et al, "Semi-Automated 3-Dimensional Intracardiac Echocardiography: Development and Initial Clinical Experience of a New System to Guide Ablation Procedures", Heart Rhythm, 3 (12), pp. 1453-1459, 2006.

(Continued)

*Primary Examiner* — Manav Seth
(74) *Attorney, Agent, or Firm* — William Kryger

(57) ABSTRACT

A system and method of imaging an imaged subject is provided. The system comprises a controller, and an imaging system including an imaging probe in communication with the controller. The imaging probe includes a transducer array operable to move through a range of motion along a first imaging path at a first speed to acquire a first set of image data. The transducer array can be operable to move through the range of motion along the first imaging path at a second speed greater than the first speed so as to acquire an update image data at a rate faster than acquisition of the first set of image data.

16 Claims, 5 Drawing Sheets

U.S. PATENT DOCUMENTS

| | | | | |
|---|---|---|---|---|
| 5,161,536 | A | * | 11/1992 | Vilkomerson et al. ......... 600/443 |
| 5,383,460 | A | * | 1/1995 | Jang et al. ...................... 600/439 |
| 5,534,874 | A | * | 7/1996 | Yujiri et al. .................... 342/351 |
| 5,612,985 | A | * | 3/1997 | Toki et al. ........................... 378/4 |
| 5,742,377 | A | * | 4/1998 | Minne et al. ..................... 355/71 |
| 5,938,602 | A | | 8/1999 | Lloyd |
| 6,350,238 | B1 | * | 2/2002 | Olstad et al. .................. 600/437 |
| 6,490,474 | B1 | | 12/2002 | Willis et al. |
| 6,514,249 | B1 | | 2/2003 | Maguire et al. |
| 6,669,635 | B2 | | 12/2003 | Kessman et al. |
| 6,689,063 | B1 | * | 2/2004 | Jensen et al. .................. 600/443 |
| 6,716,166 | B2 | | 4/2004 | Govari |
| 6,773,402 | B2 | | 8/2004 | Govari et al. |
| 7,090,639 | B2 | | 8/2006 | Govari |
| 7,156,816 | B2 | | 1/2007 | Schwartz et al. |
| 7,324,910 | B2 | * | 1/2008 | Struempler et al. ........... 702/116 |
| 2002/0005719 | A1 | | 1/2002 | Gilboa et al. |
| 2002/0026118 | A1 | | 2/2002 | Govari |
| 2002/0042571 | A1 | | 4/2002 | Gilboa et al. |
| 2003/0013958 | A1 | | 1/2003 | Govari et al. |
| 2003/0074011 | A1 | | 4/2003 | Gilboa et al. |
| 2003/0208102 | A1 | | 11/2003 | Gilboa |
| 2004/0102769 | A1 | | 5/2004 | Schwartz et al. |
| 2004/0138548 | A1 | | 7/2004 | Strommer et al. |
| 2004/0162507 | A1 | | 8/2004 | Govari |
| 2004/0162550 | A1 | | 8/2004 | Govari et al. |
| 2004/0254458 | A1 | | 12/2004 | Govari |
| 2005/0131302 | A1 | * | 6/2005 | Poland ............................ 600/459 |
| 2005/0197557 | A1 | | 9/2005 | Strommer et al. |
| 2006/0241445 | A1 | | 10/2006 | Altmann et al. |
| 2006/0253024 | A1 | | 11/2006 | Altmann et al. |
| 2006/0253029 | A1 | | 11/2006 | Altmann et al. |
| 2006/0253030 | A1 | | 11/2006 | Altmann et al. |
| 2006/0253031 | A1 | | 11/2006 | Altmann et al. |
| 2006/0253032 | A1 | | 11/2006 | Altmann et al. |
| 2007/0038088 | A1 | * | 2/2007 | Rich et al. ...................... 600/437 |
| 2007/0150238 | A1 | * | 6/2007 | Struempler et al. ........... 702/189 |

OTHER PUBLICATIONS

Proulx, T.L. et al, "Advances in Catheter-Based Ultrasound Imaging", IEEE International Ultrasonics Symposium Proceedings, 2005.

Rotger, D. et al, "Multimodal Registration of Intravascular Ultrasound Images and Angiography", Computer Vision Center Universitat Autonoma de Barcelona Bellaerra, Spain, www.cvc.uab.es/~petia/caseib2002.pdf, 2002.

Huang, X. et al, "Dynamic 3D Ultrasound and MR Image Registration of the Beating Heart", MICAI, LNCS 3750, pp. 171-178, 2005.

Martin, R. et al, "A Miniature Position and Orientation Locator for Three Dimensional Echocardiography", IEEE Proceedings on Computer in Cardiology, pp. 25-28, 1993.

Beaseley, R.A. et al, "Registration of ultrasound images", www.tgt.vanderbilt.edu/archive/registration of ultrasound images.pdf, 1999.

Leotta, D.F. et al, "Three-Dimensional Ultrasound Imaging Using Multiple Magnetic Tracking Systems and Miniature Magnetic Sensors", IEEE on Ultrasonics Symposium, pp. 1415-1418, 1995.

Pagoulatos, N. et al, "Ineractive 3-D Registration of Ultrasound and Magnetic Resonance Images Based on a Magnetic Position Sensor", IEEE on Info. Tech. in Biomedicine, vol. 3, No. 4, 1999.

"Catheter Ablation", Cleveland Clinic—Heart & Vascular Institute, http://www.clevelandclinic.org/heartcenter/pub/guide/tests/procedures/ablation.htm, Apr. 2005.

Stoll, J et al, "Passive Markers for Ultrasound Tracking of Surgical Instruments", MICCAI, LNCS 3750, pp. 41-48, 2005.

* cited by examiner

SYSTEM AND METHOD OF EXTENDED FIELD OF VIEW IMAGE ACQUISITION OF AN IMAGED SUBJECT

RELATED APPLICATIONS

This application claims priority to U.S. Provisional Application No. 60/938,445 filed on May 16, 2007, and is hereby incorporated herein by reference in its entirety.

BACKGROUND

The subject matter herein generally relates to medical imaging, and more specifically, to a system and method to navigate a tool through an imaged subject.

Image-guided surgery is a developing technology that generally provides a surgeon with a virtual roadmap into a patient's anatomy. This virtual roadmap allows the surgeon to reduce the size of entry or incision into the patient, which can minimize pain and trauma to the patient and result in shorter hospital stays. Examples of image-guided procedures include laparoscopic surgery, thoracoscopic surgery, endoscopic surgery, etc. Types of medical imaging systems, for example, computerized tomography (CT), magnetic resonance imaging (MRI), positron emission tomography (PET), ultrasound (US), radiological machines, etc., can be useful in providing static image guiding assistance to medical procedures. The above-described imaging systems can provide two-dimensional or three-dimensional images that can be displayed to provide a surgeon or clinician with an illustrative map to guide a tool (e.g., a catheter) through an area of interest of a patient's body.

When performing a medical procedure, it is desired to calibrate or align the acquired image data of the imaged subject with the tracked tool so as to navigate through the imaged subject. Yet, the sensors to track the tool and the detectors to acquire the image data may not be precisely located due to manufacturing variation. One example of application of image-guided surgery is to perform an interventional procedure to treat cardiac disorders or arrhythmias. Heart rhythm disorders or cardiac arrhythmias are a major cause of mortality and morbidity. Atrial fibrillation is one of the most common sustained cardiac arrhythmias encountered in clinical practice. Cardiac electrophysiology has evolved into a clinical tool to diagnose these cardiac arrhythmias. As will be appreciated, during electrophysiological studies, probes, such as catheters, are positioned inside the anatomy, such as the heart, and electrical recordings are made from the different chambers of the heart.

A certain conventional image-guided surgery technique used in interventional procedures includes inserting a probe, such as an imaging catheter, into a vein, such as the femoral vein. The catheter is operable to acquire image data to monitor or treat the patient. Precise guidance of the imaging catheter from the point of entry and through the vascular structure of the patient to a desired anatomical location is progressively becoming more important. Current techniques typically employ fluoroscopic imaging to monitor and guide the imaging catheter within the vascular structure of the patient.

BRIEF SUMMARY

A technical effect of the embodiments of the system and method described herein includes increasing the field of view of image data acquisition employed to generate three- or four-dimensional reconstruction of images to guide an interventional surgery procedure. Generally, as a surgeon moves the medical instrument with respect to the patient's anatomy, virtual images of the instrument or object are displayed simultaneously relative to real-time acquired image data represented in the model of the patient's anatomy. Another technical effect of the system and method described herein of tracking includes readily tracking the spatial relationship of the medical instruments or objects traveling through an operating space of patient. Yet, another technical effect of the system and method described herein includes reducing manpower, expense, and time to perform interventional procedures, thereby reducing health risks associated with long-term exposure of the subject to radiation.

According to one embodiment of the subject matter described herein, a system to image an imaged subject is provided. The system comprises a controller, and an imaging system including an imaging probe in communication with the controller. The imaging probe includes a transducer array that can be operable to move through a range of motion along a first imaging path at a first speed to acquire a first set of image data. The transducer array can be operable to move through the range of motion along the first imaging path at a second speed greater than the first speed so as to acquire an update image data at a rate faster than acquisition of the first set of image data.

According to another embodiment of the subject matter described herein, a method of image acquisition of an imaged anatomy is provided. The method comprises the steps of providing an imaging system including an imaging probe having a transducer array; rotating the transducer array about a longitudinal axis at a first speed along a first imaging path to acquire a first set of image data; rotating the transducer array about the longitudinal axis at a second speed greater than the first speed so as to acquire an update image data along the first imaging path at a rate faster than acquisition of the first set of image data along the first imaging path; and generating a display of the first set of image data combined with the update image data.

Systems and methods of varying scope are described herein. In addition to the aspects of the subject matter described in this summary, further aspects of the subject matter will become apparent by reference to the drawings and with reference to the detailed description that follows.

DETAILED DESCRIPTION

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Figure 1:
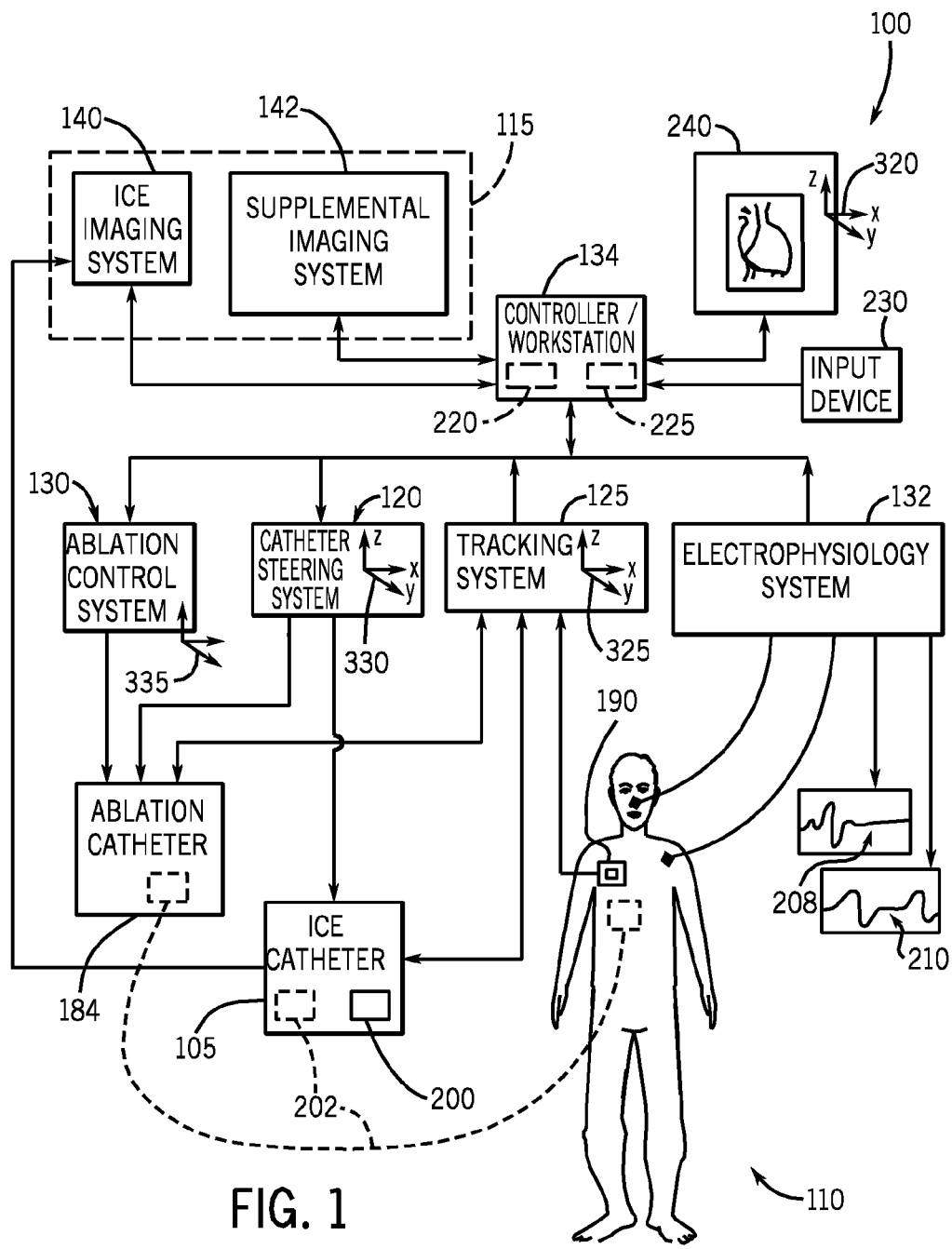
FIG. 1 illustrates a schematic diagram of an embodiment of a system of the subject matter described herein to perform image guided medical procedures on an imaged subject.
Figure 3:
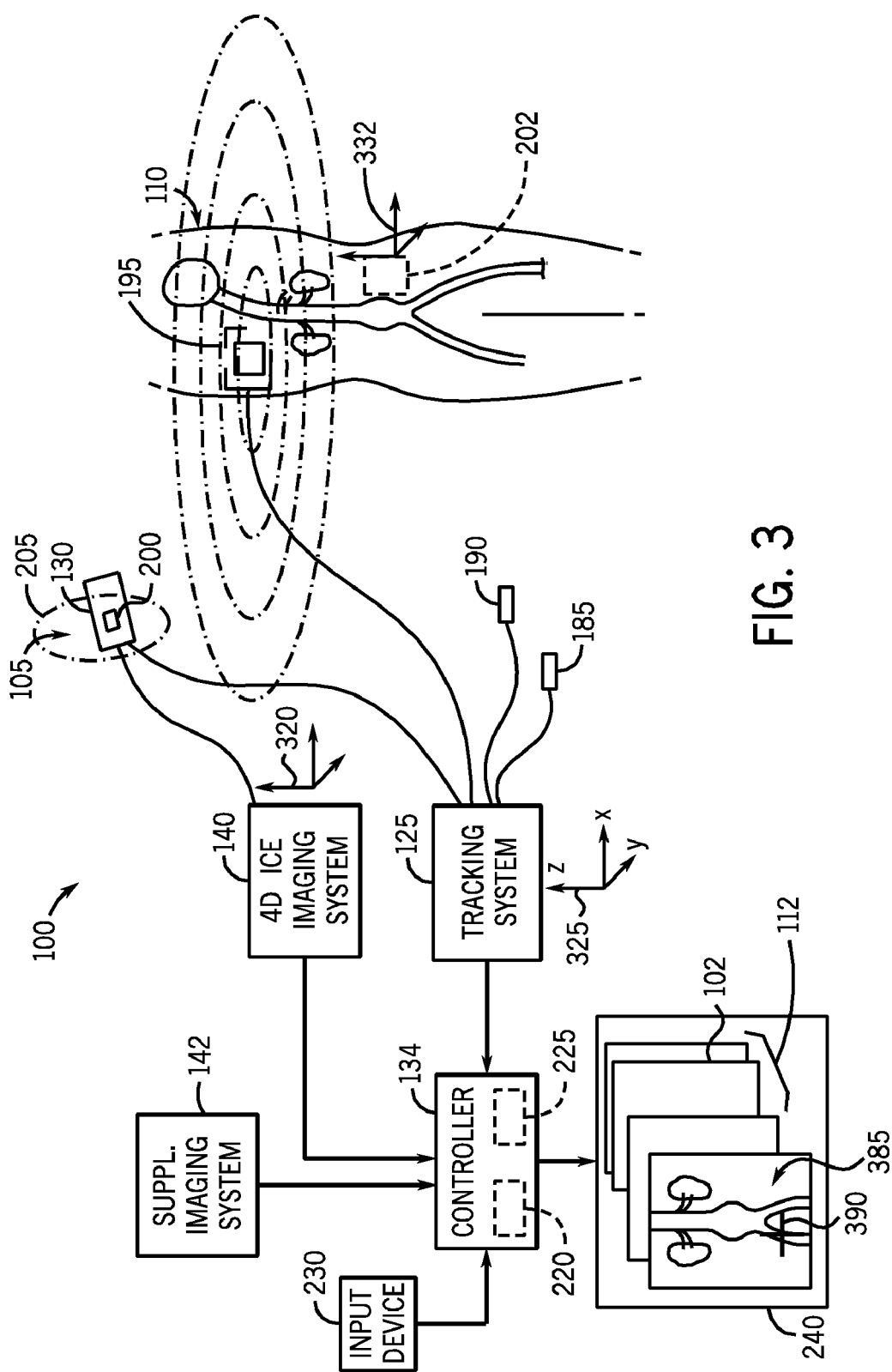
FIG. 3 illustrates a more detailed schematic diagram of a tracking system in combination with an imaging system as part of the system described in FIG. 1.

FIGS. 1 and 3 illustrate an embodiment of a system 100 operable to create a full-view three- or four-dimensional (3D or 4D) image or model from a series of generally real-time, acquired 3D or 4D image data 102 relative to a tracked position information of a probe (e.g., an imaging catheter 105) traveling through the imaged subject 110. According to one embodiment, the system 100 can be operable to acquire a series of generally real-time, partial view, 3D or 4D image data 102 while simultaneously rotating and tracking a position and orientation of the catheter 105 through the imaged subject 110. From the acquired generally real-time, partial views of 3D or 4D image data 102, a technical effect of the system 100 includes creating an illustration of a generally real-time 3D or 4D model 112 of a region of interest (e.g., a beating heart) so as to guide a surgical procedure.

An embodiment of the system 100 generally includes an image acquisition system 115, a steering system 120, a tracking system 125, an ablation system 130, and an electrophysiology system 132 (e.g., a cardiac monitor, respiratory monitor, pulse monitor, etc. or combination thereof), and a controller or workstation 134.

The image acquisition system 115 is generally operable to generate the 3D or 4D image or model 112 corresponding to an area of interest of the imaged subject 110. Examples of the image acquisition system 115 can include, but are not limited to, computed tomography (CT), magnetic resonance imaging (MRI), x-ray or radiation, positron emission tomography (PET), ultrasound (US), angiography, fluoroscopy, and the like or combination thereof. The image acquisition system 115 can be operable to generate static images acquired by static imaging detectors (e.g., CT systems, MRI systems, etc.) prior to a medical procedure, or real-time images acquired with real-time imaging detectors (e.g., angiographic systems, fluoroscopic systems, laparoscopic systems, endoscopic systems, intracardiac systems, etc.) during the medical procedure. Thus, the types of images acquired by the acquisition system 115 can be diagnostic or interventional.

One embodiment of the image acquisition system 115 includes a generally real-time, intracardiac echocardiography (ICE) imaging system 140 that employs ultrasound to acquire generally real-time, 3D or 4D ultrasound image data of the patient's anatomy and to merge the acquired image data to generate a 3D or 4D image or model 112 of the patient's anatomy relative to time, generally herein referred to as the 4D model or image 112. In accordance with another embodiment, the image acquisition system 115 is operable to fuse or combine acquired image data using above-described ICE imaging system 140 with pre-acquired or intra-operative image data or image models (e.g., 2D or 3D reconstructed image models) generated by another type of supplemental imaging system 142 (e.g., CT, MRI, PET, ultrasound, fluoroscopy, x-ray, etc. or combinations thereof).

Figure 2:
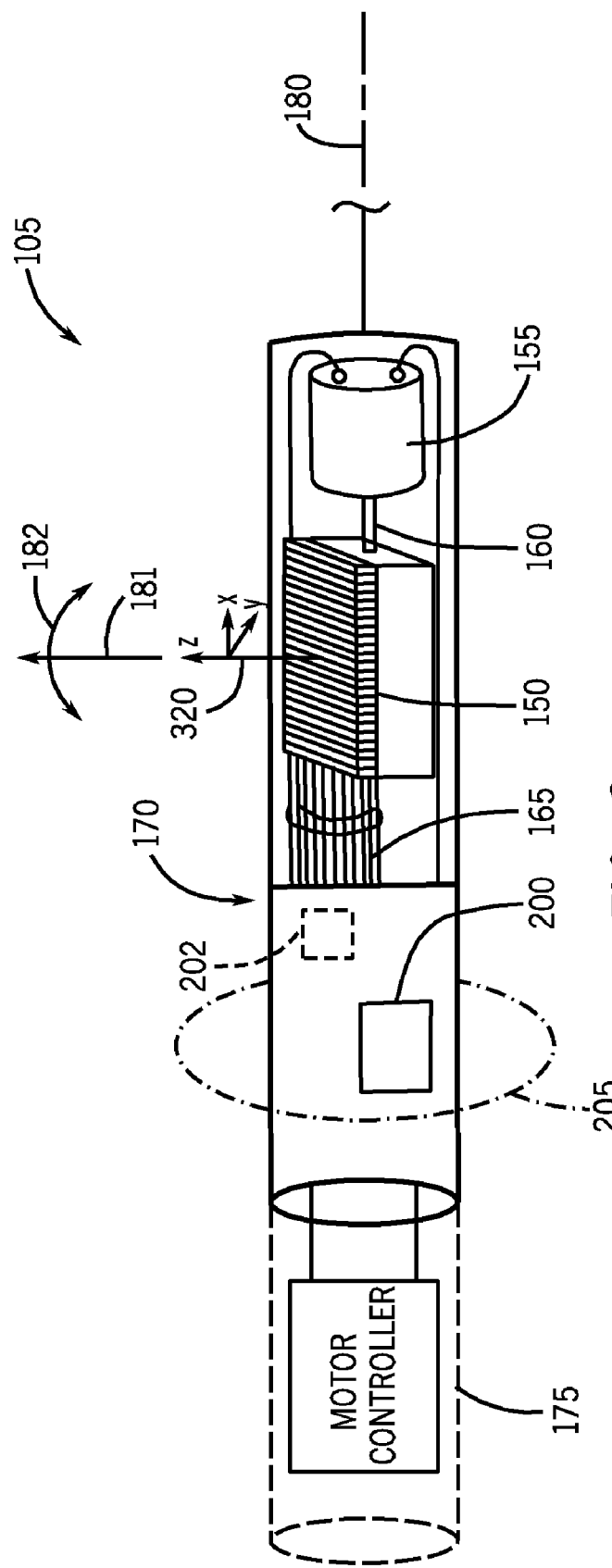
FIG. 2 illustrates a picture of a tool to travel through the imaged subject.

FIG. 2 illustrates one embodiment of the catheter 105, herein referred to as an ICE catheter 105. The illustrated embodiment of the ICE catheter 105 includes a transducer array 150, a micromotor 155, a drive shaft or other mechanical connection 160 between the micromotor 155 and the transducer array 150, an interconnect 165, and a catheter housing 170.

According to the illustrated embodiment in FIG. 2, the micromotor 155 via the drive shaft 160 generally rotates the transducer array 150. The rotational motion of the transducer array 150 is controlled by a motor control 175 of the micromotor 155. The interconnect 165 generally refers to, for example, cables and other connections coupling so as to receive and/or transmit signals between the transducer array 150 with the ICE imaging system 140 (shown in FIG. 1). An embodiment of the interconnect 165 is configured to reduce its respective torque load on the transducer array 150 and the micromotor 155.

Still referring to FIG. 2, an embodiment of the catheter housing 170 generally encloses the transducer array 150, the micromotor 155, the drive shaft 160, and the interconnect 165. The catheter housing 170 may further enclose the motor control 175 (illustrated in dashed line). The catheter housing 170 is generally of a material, size, and shape adaptable to internal imaging applications and insertion into regions of interest of the imaged subject 110. At least a portion of the catheter housing 170 that intersects the ultrasound imaging volume or scanning direction is comprised of acoustically transparent (e.g., low attenuation and scattering, acoustic impedance near that of the blood and tissue (Z~1.5M Rayl)) material. An embodiment of the space between the transducer array 150 and the housing 170 is filled with acoustic coupling fluid (e.g., water) having an acoustic impedance and sound velocity near those of blood and tissue (e.g., Z~1.5M Rayl, V~1540 m/sec).

An embodiment of the transducer array 150 is a 64-element one-dimensional array having 0.110 mm azimuth pitch, 2.5 mm elevation, and 6.5 MHz center frequency. The elements of the transducer array 150 are electronically phased in order to acquire a sector image generally parallel to a longitudinal axis 180 of the catheter housing 170. In operation, the micromotor 155 mechanically rotates the transducer array 150 about the longitudinal axis 180. The rotating transducer array 150 captures a plurality of two-dimensional images for transmission to the ICE imaging system 140 (shown in FIG. 1). As shown in FIG. 3, the ICE imaging system 140 is generally operable to assemble the sequence or succession of acquired 2D or 3D or 4D image data 102 so as to generally produce or generate 3D or 4D image or reconstructed model 112 of the imaged subject 110.

Referring to FIG. 2 again, the motor control 175 via the micromotor 155 generally regulates or controls the rate of rotation of the transducer array 150 about the longitudinal axis 180 of the ICE catheter 105. For example, the motor control 175 can instruct the micromotor 155 to rotate the transducer array 150 relatively slowly to produce the 3D reconstructed image or model 112 (See FIG. 3). Also, the motor control 175 can instruct the micromotor 155 to rotate the transducer array 150 relatively faster to produce the generally real-time, 3D or 4D reconstructed image or model. The 4D reconstructed image or model 112 can be defined to include 3D reconstructed image data correlated relative to an instant or instantaneous time of image acquisition. The motor control 175 is also generally operable to vary the direction of rotation so as to generally create an oscillatory motion of the transducer array 150. By varying the direction of rotation, the motor control 175 is operable to reduce the torque load associated with the interconnect 165, thereby enhancing the performance of the transducer array 150 to focus imaging on specific regions within the range of motion of the transducer array 150 about the longitudinal axis 180.

Referring back to FIG. 1, an embodiment of the steering system 120 is generally coupled in communication to control maneuvering (including the position or the orientation) of the ICE catheter 105. The embodiment of the system 100 can include synchronizing the steering system 120 with gated image acquisition by the ICE imaging system 140. The steering system 120 may be provided with a manual catheter steering function or an automatic catheter steering function or combination thereof. With selection of the manual steering function, the controller 134 and/or steering system 120 and/or motor controller 175 (See FIG. 2) aligns transducer array 150 and an imaging plane vector 181 (See FIG. 2) relative to the ICE catheter 105 per received instructions from the user, as well as directs the ICE catheter 105 to a target anatomical site. An embodiment of the imaging plane vector 181 (See FIG. 2) represents a central imaging direction of the path or plane that the transducer array 150 travels, moves or rotates through relative to the longitudinal axis 180. With selection of the automatic steering function, the controller 134 and/or steering system 120 and/or motor controller 175 or combination thereof estimates a displacement or a rotation angle 182 (See FIG. 2) at or less than maximum relative to a reference (e.g., imaging plane vector 181), passes position information of the ICE catheter 105 to the steering system 120, and automatically drives or positions the ICE catheter 105 and transducer array 150 to continuously follow movement of a second object (e.g., delivery of an ablation catheter 184 of the ablation system 130, moving anatomy, etc.). The reference (e.g., imaging plane vector 181 (See FIG. 2)) can vary.

Referring to FIGS. 1 and 3, the tracking system 125 is generally operable to track or detect the position of the tool or ICE catheter 105 relative to the acquired image data or 3D or 4D reconstructed image or model 112 generated by the image acquisition system 115, or relative to delivery of a second instrument or tool (e.g., ablation system 130, electrophysiology system 132).

As illustrated in FIG. 3, an embodiment of the tracking system 125 includes an array or series of microsensors or tracking elements 185, 190, 195, 200 connected (e.g., via a hard-wired or wireless connection) to communicate position data to the controller 134 (See FIG. 1). Yet, it should be understood that the number of tracking elements 185, 190, 195, 200 can vary. Referring to FIGS. 1 and 3, an embodiment of the system 100 includes intraoperative tracking and guidance in the delivery of the at least one catheter 184 of the ablation system 130 by employing a hybrid electromagnetic and ultrasound positioning technique. The hybrid electromagnetic/ultrasound positioning technique facilitates dynamic tracking by locating tracking elements or dynamic references 185, 190, 195, 200, alone or in combination with ultrasound markers 202 (e.g., comprised of metallic objects such brass balls, wire, etc.). The ultrasonic markers 202 may be active (e.g., illustrated in dashed line located at catheters 105 and 184) or passive targets (e.g., illustrated in dashed line at imaged anatomy of subject 110). An embodiment of the ultrasound markers 202 can be located at the ICE catheter 105 and/or ablation catheter 184 so as to be identified or detected in acquired image data by supplemental imaging system 142 and/or the ICE imaging system 140. The tracking system 125 can be configured to selectively switch between tracking relative to electromagnetic tracking elements 185, 190, 195, 200 or ultrasound markers 202 or simultaneously track both.

For sake of example in referring to FIGS. 1 and 3, assume the series of tracking elements 185, 190, 195, 200 includes a combination of transmitters or dynamic references 185 and 190 in communication or coupled (e.g., RF signal, optically, electromagnetically, etc.) with one or more receivers 195 and 200. The number and type transmitters in combination with receivers can vary. Either the transmitters 185 and 190 or the receivers 195 and 200 can define the reference of the spatial relation of the tracking elements 185, 190, 195, 200 relative to one another. An embodiment of one of the receivers 195 represents a dynamic reference at the imaged anatomy of the subject 110. An embodiment of the system 100 is operable to register or calibrate the location (e.g., position and/or orientation) of the tracking elements 185, 190, 195, 200 relative to the acquired imaging data by the image acquisition system 115, and operable to generate a graphic representation suitable to visualize the location of the tracking elements 185, 190, 195, 200 relative to the acquired image data.

The tracking elements 185, 190, 195, 200 generally enable a surgeon to continually track the position and orientation of the catheters 105 or 184 during surgery. The tracking elements 185, 190, 195, 200 may be passively powered, powered by an external power source, or powered by an internal battery. One embodiment of one or more of the tracking elements or microsensors 185, 190, 195, 200 includes electromagnetic (EM) field generators having microcoils operable to generate a magnetic field, and one or more of the tracking elements 185, 190, 195, 200 include an EM field sensor operable to detect an EM field. For example, assume tracking elements 185 and 190 include a EM field sensor operable such that when positioned into proximity within the EM field generated by the other tracking elements 195 or 200 is operable to calculate or measure the position and orientation of the tracking elements 195 or 200 in real-time (e.g., continuously), or vice versa, to calculate the position and orientation of the tracking elements 185 or 190.

For example, tracking elements 185 and 190 can include EM field generators attached to the subject 110 and operable to generate an EM field, and assume that tracking element 195 or 200 includes an EM sensor or array operable in combination with the EM generators 185 and 190 to generate tracking data of the tracking elements 185, 190 attached to the patient 110 relative to the microsensor 195 or 200 in real-time (e.g., continuously). According to one embodiment of the series of tracking elements 185, 190, 195, 200, one is an EM field receiver and a remainder are EM field generators. The EM field receiver may include an array having at least one coil or at least one coil pair and electronics for digitizing magnetic field measurements detected by the receiver array. It should, however, be understood that according to alternate embodiments, the number and combination of EM field receivers and EM field generators can vary.

The field measurements generated or tracked by the tracking elements 185, 190, 195, 200 can be used to calculate the position and orientation of one another and attached instruments (e.g., catheters 105 or 184) according to any suitable method or technique. In one embodiment, the field measurements tracked by the combination of tracking elements 185, 190, 195, 200 can be digitized into signals for transmission (e.g., wireless, or wired) to the tracking system 125 or controller 134. The controller 134 is generally operable to register the position and orientation information of the one or more tracking elements 185, 190, 195, 200 relative to the acquired imaging data from ICE imaging system 140 or other supplemental imaging system 142. Thereby, the system 100 is operable to visualize or illustrate the location of the one or more tracking elements 185, 190, 195, 200 or attached catheters 105 or 184 relative to pre-acquired image data or real-time image data acquired by the image acquisition system 115.

Still referring to FIGS. 1 and 3, an embodiment of the tracking system 125 includes the tracking element 200 located at the ICE catheter 105. The tracking element 200 is in communication with the receiver 195. This embodiment of the tracking element 200 includes a transmitter that comprises a series of coils that define the orientation or alignment of the ICE catheter 105 about the rotational axis (generally aligned along the longitudinal axis 180 in FIG. 2) of the ICE catheter 105. Referring to FIG. 2, the tracking element 200 can be located integrally with the ICE catheter 105 and can be generally operable to generate or transmit a magnetic field 205 to be detected by the receiver 195 of the tracking system 125. In response to passing through the magnetic field 205, the receiver 195 generates a signal representative of a spatial relation and orientation of the receiver 195 or other reference relative to the transmitter 200. Yet, it should be understood that the type or mode of coupling, link or communication (e.g., RF signal, infrared light, magnetic field, electrical potential, etc.) operable to measure the spatial relation varies. The spatial relation and orientation of the tracking element 200 is mechanically pre-defined or measured in relation relative to a feature (e.g., a tip) of the ICE catheter 105. Thereby, the tracking system 125 is operable to track the position and orientation of the ICE catheter 105 navigating through the imaged subject 110.

An embodiment of the tracking elements 185, 190, or 200 can include a plurality of coils (e.g., Hemholtz coils) operable to generate a magnetic gradient field to be detected by the receiver 195 of the tracking system 125 and which defines an orientation of the ICE catheter 105. The receiver 195 can include at least one conductive loop operable to generate an electric signal indicative of spatial relation and orientation relative to the magnetic field generated by the tracking elements 185, 190 and 200.

Referring now to FIG. 1, an embodiment of the ablation system 130 includes the ablation catheter 184 that is operable to work in combination with the ICE catheter 105 of the ICE imaging system 140 to deliver ablation energy to ablate or end electrical activity of tissue of the imaged subject 110. An embodiment of the ICE catheter 105 can include or be integrated with the ablation catheter 184 or be independent thereof. An embodiment of the ablation catheter 184 can include one of the tracking elements 185, 190 of the tracking system 125 described above to track or guide intra-operative delivery of ablation energy to the imaged subject 110. Alternatively or in addition, the ablation catheter 184 can include ultrasound markers 202 operable to be detected from the acquired ultrasound image data generated by the ICE imaging system 140. The ablation system 130 is generally operable to manage the ablation energy delivery to an ablation catheter 184 relative to the acquired image data and tracked position data.

An embodiment of an electrophysiological system(s) 132 is connected in communication with the ICE imaging system 140, and is generally operable to track or monitor or acquire data of the cardiac cycle 208 or respiratory cycle 210 of imaged subject 110. Data acquisition can be correlated to the gated acquisition or otherwise acquired image data, or correlated relative to generated 3D or 4D models 112 created by the image acquisition system 115.

Still referring FIG. 1, the controller or workstation computer 134 is generally connected in communication with and controls the image acquisition system 115 (e.g., the ICE imaging system 140 or supplemental imaging system 142), the steering system 120, the tracking system 125, the ablation system 130, and the electrophysiology system 132 so as to enable each to be in synchronization with one another and to enable the data acquired therefrom to produce or generate a full-view 3D or 4D ICE model 112 (See FIG. 3) of the imaged anatomy.

An embodiment of the controller 134 includes a processor 220 in communication with a memory 225. The processor 220 can be arranged independent of or integrated with the memory 225. Although the processor 220 and memory 225 are described located at the controller 134, it should be understood that the processor 220 or memory 225 or portion thereof can be located at image acquisition system 115, the steering system 120, the tracking system 125, the ablation system 130 or the electrophysiology system 132 or combination thereof.

The processor 220 is generally operable to execute the program instructions representative of acts or steps described herein and stored in the memory 225. The processor 220 can also be capable of receiving input data or information or communicating output data. Examples of the processor 220 can include a central processing unit of a desktop computer, a microprocessor, a microcontroller, or programmable logic controller (PLC), or the like or combinations thereof.

An embodiment of the memory 225 generally comprises one or more computer-readable media operable to store a plurality of computer-readable program instructions for execution by the processor 220. The memory 225 can also be operable to store data generated or received by the controller 134. By way of example, such media may comprise RAM, ROM, PROM, EPROM, EEPROM, Flash, CD-ROM, DVD, or other known computer-readable media or combinations thereof which can be used to carry or store desired program code in the form of instructions or data structures and which can be accessed by a general purpose or special purpose computer or other machine with a processor. When information is transferred or provided over a network or another communications connection (either hardwired, wireless, or a combination of hardwired or wireless) to a machine or remote computer, the remote computer properly views the connection as a computer-readable medium. Thus, any such a connection is properly termed a computer-readable medium.

Still referring to FIG. 1, the controller 134 further includes or is in communication with an input device 230 and an output device 240. The input device 230 can be generally operable to receive and communicate information or data from a user to the controller 210. The input device 230 can include a mouse device, pointer, keyboard, touch screen, microphone, or other like device or combination thereof capable of receiving a user directive. The output device 240 is generally operable to illustrate output data for viewing by the user. An embodiment of the output device 240 can be operable to simultaneously illustrate or fuse static or real-time image data generated by the image acquisition system 115 (e.g., the ICE imaging system 140 or supplemental imaging system 142) with tracking data generated by the tracking system 125. The output device 240 is capable of illustrating two-dimensional, three-dimensional, and/or four-dimensional image data or combinations thereof through shading, coloring, and/or the like. Examples of the output device 240 include a cathode ray monitor, a liquid crystal display (LCD) monitor, a touch-screen monitor, a plasma monitor, or the like or combination thereof.

Figure 4:
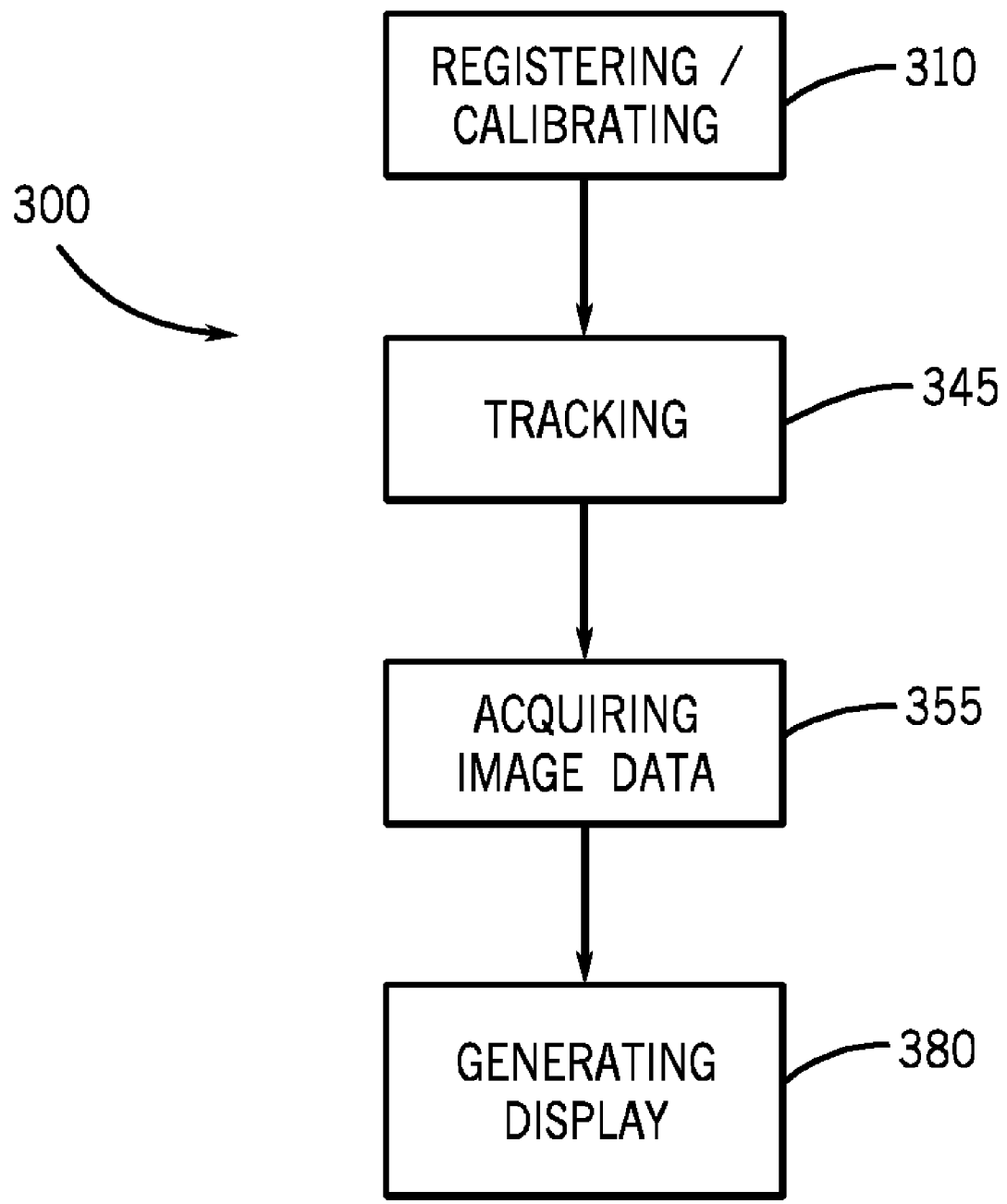
FIG. 4 shows an embodiment of a method of performing an image-guided procedure via the system of FIG. 1.
Figure 5:
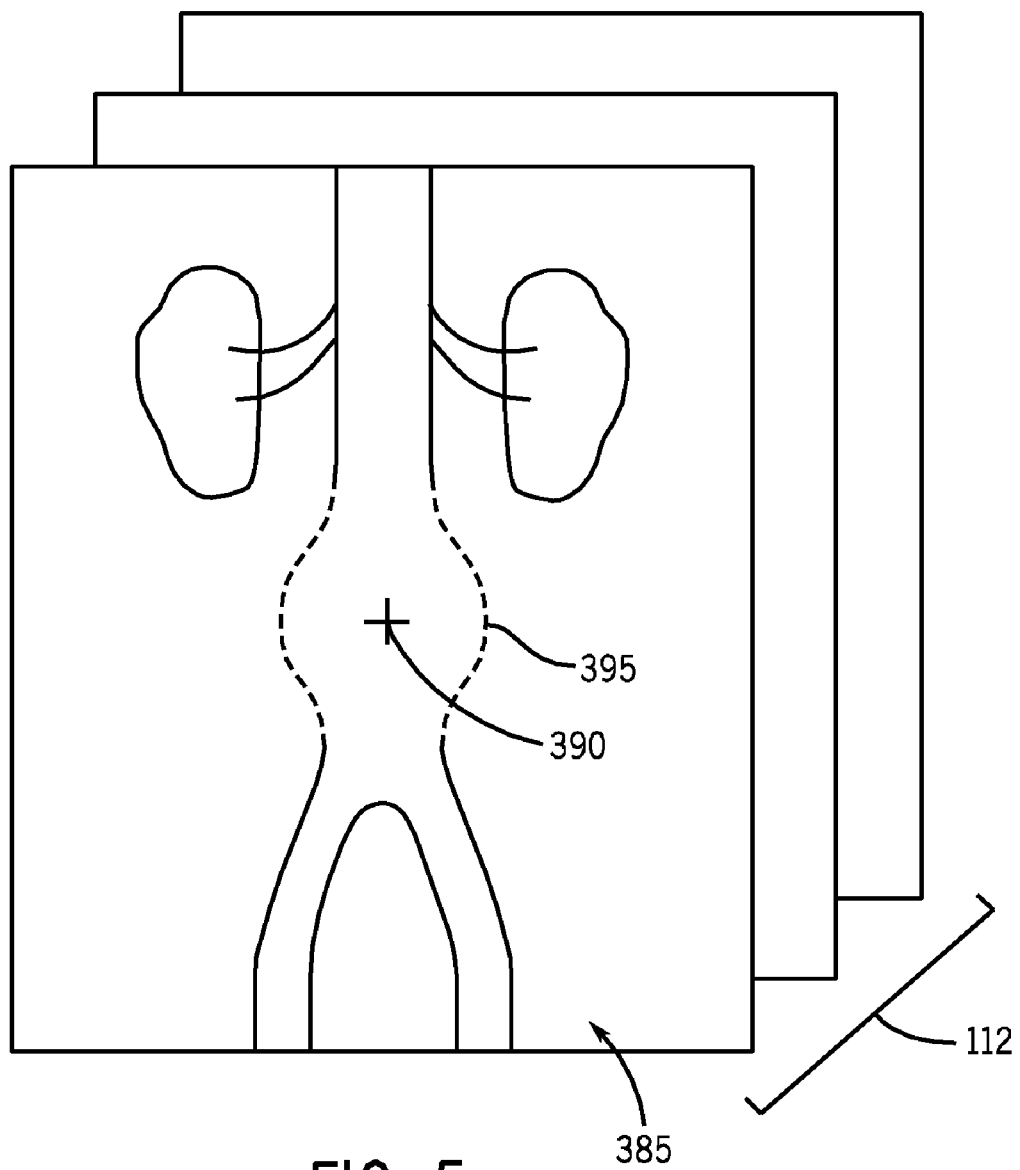
FIG. 5 shows an embodiment of an illustration of fast updated, reduced field of view image data in combination with large field of view imaged data employing the system of FIG. 1.

Having provided a description of the general construction of the system 100, the following is a description of a method 300 (see FIG. 4) of operation of the system 100 in relation to the imaged subject 110. Although an exemplary embodiment of the method 300 is discussed below, it should be understood that one or more acts or steps comprising the method 300 could be omitted or added. It should also be understood that one or more of the acts can be performed simultaneously or at least substantially simultaneously, and the sequence of the acts can vary. Furthermore, it is embodied that at least several of the following steps or acts can be represented as a series of computer-readable program instructions to be stored in the memory 225 of the controller 210 for execution by the processor 220 or one or more of the image acquisition system 115, the steering system 120, the tracking system 125, the ablation system 130, the electrophysiology system 132, or a remote computer station connected thereto via a network (wireless or wired).

The controller 134 via communication with the tracking system 125 is operable to track movement of the ICE catheter 105 in accordance with known mathematical algorithms programmed as program instructions of software for execution by the processor 220 of the controller 134 or by the tracking system 125. An exemplary navigation software is INSTATRAK® as manufactured by the GENERAL ELECTRIC® Corporation, NAVIVISION® as manufactured by SIEMENS®, and BRAINLAB®.

As illustrated in FIGS. 1 through 4, the method 300 includes a step of registering 310 a reference frame 320 of the ICE imaging system 140 with one or more of the group comprising: a reference frame 325 of the tracking system 125, a reference frame 330 of the steering system 120, a reference frame 335 of the ablation system 130, or a reference time frame of the electrophysiological system(s) (e.g., cardiac monitoring system, respiratory monitoring system, etc.) 132.

The embodiment of the method 300 further includes a step 345 of tracking (e.g., via the tracking system 125) a position or location of the at least one catheter 105 or 184 relative to the acquired image data. According to one embodiment of the method 300, at least one catheter 105 or 184 is integrated with one of the plurality of hybrid tracking elements 185, 190, 195, 200 and/or ultrasonic markers 202. The tracking elements 185, 190, 195, 200 and ultrasonic markers 202 can both be located and rigidly mounted on the at least one instrument catheter 105 or 184. A computer image-processing program is operable to detect and mark positions of the ultrasonic markers 202 relative to the generated 3D or 4D ICE image model 112.

The controller 134 can be generally operable to align positions of the ultrasonic markers 202 with a tracking coordinate reference frame or coordinate system 325. This registration information may be used for the alignment (calibration) between the tracking reference frame or coordinate system 325 and an ultrasonic marker reference frame or coordinate system 332 (See FIG. 3) relative to the imaging reference frame or coordinate system 320. This information may also be used for detecting the presence of electromagnetic distortion or tracking inaccuracy.

An embodiment of the method 300 further includes a step 355 of acquiring image data (e.g., scan) of the anatomy of interest of the imaged subject 110. An embodiment of the step of acquiring image data includes acquiring the series of partial-views 102 of 3D or 4D image data while rotating the transducer array 150 around the longitudinal axis 180. The image acquisition step 355 can include synchronizing or gating a sequence of image acquisition relative to cardiac and respiratory cycle information 208, 210 measured by the electrophysiology system 132.

One embodiment of the ICE catheter 105 can acquire image data without moving the position of the ICE catheter 105 relative to imaged subject 110. The transducer array 150 of the ICE catheter 105 may have about a 90-degree azimuth field of view (FOV). The micromotor 155 can rotate the transducer array 150 within the ICE catheter 105 through more than about a 60-degree (perhaps as much as 180° or more) angular range of motion about the longitudinal axis 180.

An embodiment of the step 355 of acquiring a large FOV image data can include moving the catheter 105 to multiple locations. The ICE catheter 105 can be instructed via the controller 134 to acquire the large-FOV image data with one slow rotation or scan of the transducer array 150 at multiple locations. The controller 134 can instruct the ICE catheter 105 to acquire the series of partial view, 3D or 4D image data 102 at discrete locations or acquire continuously during movement of the ICE catheter 105. The image acquisition system 115 can integrate or combine the series of partial view 3D or 4D image data 102 according to tracking data of movement of the catheter 105 or ablation catheter 184 to create the larger FOV image or model (e.g., 3D or 4D model 112) of the imaged anatomy.

According to one embodiment of the system 100, the ICE catheter 105 can perform the large FOV image acquisition in combination with fast or generally real-time updates of reduced FOV image data. The ICE catheter 105 can be instructed to acquire fast updates of reduced-FOV image data with multiple fast rotations or scans of the transducer array 150. For fast updates of the reduced FOV image acquisition, the controller 134 can instruct the ICE catheter 105 to move or rotate at a less than maximum range of motion 182 of the transducer array 150, relative to the range of motion of large FOV image acquisition. For example, the ICE catheter 105 can be instructed to acquire image data over multiple fast rotations or scans over a reduced range of motion of the transducer array 150 correlated or synchronized relative to cardiac or respiratory cycle information (e.g., ECG or respiratory cycles 208, 210) acquired by the electrophysiology system 132.

The embodiment of the ICE catheter 105 can include the tracking element 200 (e.g., electromagnetic coils or electrodes or other tracking technology) or ultrasound marker 202 operable such that the tracking system 125 can calculate the position and orientation (about six degrees of freedom) of the catheter 105. The tracking information may be used in combination with the registering step 310 described above to align the series of partial view 3D or 4D images 102 to create the larger 3D or 4D image or model 112 with an extended or larger FOV. The controller 134 analyzes the tracking information correlated to the acquired image data to align fast updates of generally real-time, reduced-FOV 3D or 4D images 102 with the larger FOV 3D or 4D image or model 112.

The ICE catheter 105 can also be operable to intermittently alternate between large FOV image acquisition associated with rotation or scan of the transducer array 150 across a range of motion, and reduced FOV image acquisition associated with fast rotation or motion relative thereto. Another embodiment of the ICE catheter 105 can be instructed to acquire large FOV image data intermittently or interleaved with fast-updates of reduced-FOV image acquisition. For example, via instructions from the controller 134, the ICE catheter 105 can perform reduced FOV image acquisition with fast updates for an identified target or region of interest of the imaged anatomy, while performing large FOV image acquisition over a remainder of the imaged anatomy. The target or region of interest can be identified by the operator via the input device 230, or be identified by the controller 134 according to a measure of the change in image data. For example, the imaging system 115 could analyze the recently acquired image data to identify anatomic boundaries or structures (vessels, chambers, valves) and other structures (e.g., a therapy catheter 184) or features in the imaged FOV. The imaging system 115 or controller 134 could specifically identify those structures that meet specified criteria, such as moving at a predetermined rate (e.g., minimum or maximum change in acquired image data per period of time, structure having fastest speed, etc.) or through a particular distance, then the controller 134 could direct the ICE catheter 105 to perform fast-update, reduced-FOV imaging of those specific structures or image features. Fast-update, reduced-FOV image can be merged with large-FOV image, so that most of the combined image is stable or updates slowly, but a target portion region of interest updates rapidly. In another example, the fast-update and large-FOV images can be displayed separately or independently relative to other acquired image data. If separate, the reduced FOV of the fast-update image can be shown on the large-FOV image as an outline or overlay.

The ICE catheter 105 can be operable to perform a partial scan of large FOV image acquisition over a portion of the range of motion 182 of the transducer array 150, combined with a partial scan of reduced FOV image acquisition relative thereto over a remainder of the portion of the range of motion 182 of the transducer array 150. Thus, the micromotor 155 is operable to change the speed or rate of rotation or motion of the transducer array 150 across a single scan or range of motion in a single direction or upon movement in a return direction. The change in speed or rate of rotation of the motion of the transducer array 150 can be controlled according to predetermined values stored at the controller 134, or can be controlled manually in an intermittent manner or basis according to values received via the input device 230.

In another example, the controller 134 can instruct the ICE imaging system 140 and/or the motor controller 175 and/or the transducer array 150 of the ICE catheter 105 to begin with large FOV image acquisition at a slow speed in a first direction up to a first point along the range of motion of the transducer array 150, then proceed with reduced FOV image acquisition to obtain fast updates (e.g., one or more reduced FOV fast scans with each slower large FOV scan) between the first point and a second point along the range of motion of the transducer array 150 range of motion, and continue with image acquisition at a slower rate from the second point for the remainder of the range of motion of the transducer array 150. An embodiment of the step 355 can include any combination of reduced FOV or large FOV image acquisition described above.

One embodiment of the ICE catheter 105 and/or the ICE imaging system 140 can be instructed to acquire image data in response to a request received from an operator via the input device 230. Another embodiment of the ICE catheter 105 and/or the ICE imaging system 140 can be instructed via the controller 134 to automatically acquire image data at specified time intervals. Yet another embodiment of the ICE catheter 105 and/or the ICE imaging system 140 can be instructed to acquire fast updates of image data at an increased rate or speed of rotation in response to detecting a predetermined measure of change in acquired image data indicative of a need to update. For example, the measure of change in image data can be measured or detected by the image acquisition system 115 relative to a gray-scale intensity of prior acquired generally real-time, partial view, 3D or 4D image data 102 of a common point of the imaged subject 110, or relative to preoperative image data (e.g., CT images, MR images, ultrasound images, fluoroscopic images, etc.) of the common point of the imaged subject 110, or relative to changes in measured locations of detected boundaries of imaged anatomy.

For example, the controller 134 can receive instructions via the input device 230 to command the ICE catheter 105 and/or the ICE imaging system 140 to acquire fast-updates of the portion of the large-FOV image, or the controller 134 can command the ICE catheter 105 and/or the ICE imaging system 140 to acquire fast updates of the reduced FOV image data according to presets or image analysis (e.g., to identify valves or other rapidly-moving objects). If the fast-update FOV includes a separate diagnostic feature or object (e.g., therapy catheter 184) that moves independent of the general anatomy of the imaged subject 110, the fast-update FOV could be made to automatically move with movement of the feature or object. The image acquisition system 115 can perform image analysis to identify the position and motion of the moving feature or object (e.g., therapy catheter 184) and direct the fast-update FOV to follow the tracked movement accordingly. The moving feature or object can include an ultrasound transponder or other features to enhance identification or detection of the object's echogenicity. By tracking the moving object or feature with the tracking system 125 and registering the image coordinate system 320 of the image acquisition system 115 relative to the tracking coordinate system 325 of the tracking system 125, the direction (e.g., the imaging plane vector 181) of the fast-update FOV image acquisition can be directed toward the tracked position or movement of the object (e.g., therapy catheter 184).

Yet, the tracking system 125 is not required to track movement, and instead image processing can be performed to track movement. According to another embodiment, the tracking system 125 may not track the position or orientation of the ICE catheter 105. The image acquisition system 115 and/or controller 134 can assemble the series of acquired partial view 3D or 4D image data 102 to form the full view image or model 112 by matching of speckle, boundaries, and other features identified in the image data.

Referring to FIGS. 1 through 5, an embodiment of step 380 includes creating a display 385 of the acquired real-time, partial views of 3D or 4D ICE image data 102 of the anatomical structure in combination with one or more of the following: graphic representation(s) 390 of the locations and identifications of the ICE catheter 105 or ablation catheter 184; a graphic representation of the imaging plane vector 181 showing the general direction of the FOV of the ICE catheter 105; selection of a target anatomical site (e.g., via input instructions from the user) at the graphically illustrated surface of the generated 3D or 4D model 112 of the imaged anatomy. An embodiment of step 380 can further include creating a graphic illustration of a region of fast update image data relative to large FOV image data (illustrated in dashed line and by reference 395), a distance between a tip of the catheter 105 and the anatomical surface, a display of the path of the ICE catheter 105 or ablation catheter 184 delivery to the target anatomical site, or a display of the cardiac and respiratory cycles 208, 210 synchronized relative to a point of time of acquisition of the displayed image data. The type of graphic illustration to distinguish fast updates of reduced FOV image data (e.g., different color, opacity, boundary pattern, etc.) relative to large FOV image data can vary.

The technical effect of an increased FOV of image acquisition obtained with the image acquisition system 115 enables operators (e.g., physicians) to see both the ICE catheter 105 or ablation catheter 184 and the targeted anatomy in the same acquired image scan, without continuous tweaking of the ICE catheter 105 to keep the image aligned to the therapy catheter 184 and imaged anatomy. With the system 100 and method 300 of extended FOV image acquisition described herein, the system 100 can create or generate in near-real-time illustration of the full-view chamber anatomy information without a need to acquire expensive pre-case or pre-operative MR or CT studies. The extended FOV image, showing a large portion of the targeted chamber or organ, provides a reference or context to help the operator understand the location, orientation, and anatomy of the fast-update reduced-FOV image and effectively and efficiently direct the diagnostic or therapy catheter 184 to the desired anatomic site(s). In addition, the extended FOV can be combined with automatic targeting of fast-update FOV image acquisition that greatly reduces the need for manual maneuvering of the ICE catheter 105 during performance of a clinical procedure.

Embodiments of the subject matter described herein include method steps which can be implemented in one embodiment by a program product including machine-executable instructions, such as program code, for example in the form of program modules executed by machines in networked environments. Generally, program modules include routines, programs, objects, components, data structures, etc. that perform particular tasks or implement particular abstract data types. Machine-executable instructions, associated data structures, and program modules represent examples of computer program code for executing steps of the methods disclosed herein. The particular sequence of such computer- or processor-executable instructions or associated data structures represent examples of corresponding acts for implementing the functions described in such steps.

Embodiments of the subject matter described herein may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, minicomputers, mainframe computers, and the like. Embodiments of the subject matter described herein may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

This written description uses examples to disclose the subject matter, including the best mode, and also to enable any person skilled in the art to make and use the subject matter described herein. Accordingly, the foregoing description has been presented for purposes of illustration and description, and is not intended to be exhaustive or to limit the subject matter to the precise form disclosed, and modifications and variations are possible in light of the above teachings or may be acquired from practice of the subject matter described herein. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A system to acquire an image of an imaged subject, comprising:
   a controller; and
   an imaging system including an imaging probe in communication with the controller, the imaging probe having a transducer array operable to move through a range of motion along a first imaging path at a first speed to acquire a first set of image data, and the transducer array operable to move through the range of motion along the first imaging path at a second speed greater than the first speed so as to acquire an update image data at a rate faster than acquisition of the first set of image data.

2. The system of claim 1, further comprising a tracking system in communication with the controller, the tracking system having a tracking element integrated with the imaging probe, wherein the controller registers a location of acquisition of the first set of image data with a location of acquisition of the update image data, and wherein the controller combines the first set of image data with the update image data.

3. The system of claim 1, further comprising a tracking system in communication with the controller, the tracking system having a tracking element integrated with the imaging probe, wherein the controller registers the first set of image data with the update image data, and wherein the controller overlays the first set of image data with the update image data.

4. The system of claim 1, further comprising a tracking system in communication with the controller, the tracking system having a tracking element located at a second instrument moving independently of the imaging probe, wherein the controller instructs the transducer array to acquire the update data in a direction of movement of the second instrument as tracked by the tracking system.

5. The system of claim 1, wherein the controller instructs the imaging probe to perform image acquisition intermittently at the first speed and the second at specified time intervals.

6. The system of claim 1, wherein the controller instructs the imaging probe to acquire a second set of update image data of the acquired first set of image data in response to detecting a predetermined measure of change between sets of prior acquired image data.

7. The system of claim 1, wherein the controller instructs movement of the transducer array to acquire update image data at the second speed over a portion less than the range of motion of the transducer array to acquire the first set of image data.

8. The system of claim 1, wherein the controller instructs the transducer array to acquire image data intermittently between the first and second speeds dependent on one of the group comprising a tracked cardiac cycle and a tracked respiratory cycle.

9. A method of image acquisition of an imaged anatomy, the method comprising the steps of:
   providing an imaging system including an imaging probe having a transducer array;
   rotating the transducer array about a longitudinal axis at a first speed along a first imaging path to acquire a first set of image data;
   rotating the transducer array about the longitudinal axis at a second speed greater than the first speed so as to acquire an update image data along the first imaging path at a rate faster than acquisition of the first set of image data along the first imaging path; and
   generating a display of the first set of image data combined with the update image data.

10. The method of claim 9, further comprising the step of:
    tracking a position of the imaging probe;
    registering the first set of image data with the update image data; and
    combining the update image data into the first set of image data.

11. The method of claim 9, further comprising the step of:
    tracking a position of the imaging probe;
    registering a location of acquisition of the first set of image data with a location of acquisition of the update image data; and overlaying the first set of image data with the update image data.

12. The method of claim 9, further comprising the step of: detecting a direction of movement of a second instrument moving independently of the imaging probe, wherein the rotating step at the second speed includes acquiring the update image data at the second speed in the direction of movement of the second instrument.

13. The method of claim 9, wherein the rotating steps at the first and second speeds include acquiring the first set of image data at the first speed intermittently at specified time intervals with acquiring the update image data at the second speed.

14. The method of claim 9, wherein the rotating step at the second speed is to acquire a second set of update data in response to detecting a predetermined measure of change between prior acquired sets of image data.

15. The method of claim 9, wherein the controller instructs movement of the transducer array to acquire update image data at the second speed over a portion less than the range of motion of the transducer array to acquire the first set of image data.

16. The method of claim 9, further including the step of: instructing the transducer array to acquire the image data intermittently between the first and second speeds dependent on one of the group comprising a tracked cardiac cycle and a tracked respiratory cycle.

* * * * *